United States Patent
Eisner

(10) Patent No.: US 7,118,700 B2
(45) Date of Patent: Oct. 10, 2006

(54) METHOD FOR INHIBITING ALGAE GROWTH IN WATER TANKS AND APPARATUS THEREFOR

(75) Inventor: Neil Eisner, St. Brieux (CA)

(73) Assignee: Bourgault Industries Ltd., St. Brieux (CA)

( * ) Notice: Subject to any disclaimer, the term of this patent is extended or adjusted under 35 U.S.C. 154(b) by 408 days.

(21) Appl. No.: 10/456,866

(22) Filed: Jun. 6, 2003

(65) Prior Publication Data

US 2004/0247805 A1 Dec. 9, 2004

(51) Int. Cl.
*B28B 1/02* (2006.01)

(52) U.S. Cl. .................. 264/310; 220/62.22; 220/560; 220/565; 220/567; 264/311; 264/312

(58) Field of Classification Search ............... 428/34.1, 428/35.7; 220/62.22, 565, 567, 660; 264/310, 264/311, 312

See application file for complete search history.

(56) References Cited

U.S. PATENT DOCUMENTS 3,735,895 A * 5/1973 Roper .................. 220/565
5,547,096 A * 8/1996 Kleyn .................. 220/4.14

FOREIGN PATENT DOCUMENTS

JP 1199884 8/1989

* cited by examiner

*Primary Examiner*—Nasser Ahmad
(74) *Attorney, Agent, or Firm*—Frost Brown Todd LLC

(57) ABSTRACT

A method of inhibiting the growth of algae and like organisms in plastic water tanks exposed to sunlight comprises providing an outer tank surface operative to reflect off a substantial portion of sunlight that hits the tank off the outer tank surface; and providing an opaque inner tank layer operative to substantially prevent sunlight passing through the outer tank surface from entering an interior of the tank. A two layer tank is provided comprising a light colored outer layer and a dark sun-blocking inner layer, and is conveniently made by a rotational molding process.

4 Claims, 1 Drawing Sheet

METHOD FOR INHIBITING ALGAE GROWTH IN WATER TANKS AND APPARATUS THEREFOR

This invention is in the field of tanks, and in particular such tanks for storing water.

BACKGROUND OF THE INVENTION

Plastic tanks are widely used for liquid storage because they are economical, lightweight, durable and resistant to corrosion & chemicals. In agriculture, industry and residential applications, plastic tanks are often used for the storage of water for household use, animal consumption and use in agricultural operations such as chemical crop spraying.

In the manufacture of molded plastic tanks for liquid storage, the use of unpigmented or light colored resins is often favored. Costs and process complexities associated with the use of pigments can be reduced or eliminated. A further significant advantage of tanks with a light colored exterior is that they do not absorb heat from sunlight to the extent that a dark colored tank does, but rather reflect a substantial portion off the outer surface. Thus a light colored tank is less susceptible to sunlight-induced heating and softening of the plastic. A light colored tank stays cooler in the sun and as a result the wall thickness can be reduced compared to a dark colored tank while retaining its structure.

Under sunlight-induced heating, a dark colored tank may seriously deform or collapse under its own weight when empty, or under the stress of retaining means when tied down for transport. Prevention of such deformation or collapse is conventionally accomplished through the use of structural stiffening provided by increased wall thickness or reinforcing ribs. However, the use of additional material renders a tank heavier and more costly, and reinforcing ribs require more costly and complex molds, which also increases the cost of the tank.

A significant drawback of a light colored plastic tank used for water storage is that the tank walls are translucent. Sunlight can pass through the wall of the tank and promote the growth of algae in water stored in the tank. Such tanks are not always completely drained between uses, and algae growth in a small amount of water retained in the tank over a significant period of time can be considerable.

This algae growth is highly undesirable. Such tanks are commonly used to haul and store water for human and animal consumption, water for household use, and water for agricultural chemical spraying. Such applications require relatively pure and uncontaminated water. Not only can algae be toxic to animals and humans, but it plugs spraying equipment and can interfere with the action of agricultural chemicals.

Plastic water tanks are commonly manufactured by rotational molding processes. It is known in the rotational molding art to provide an article with an inner layer of one plastic material and an outer layer of a different plastic material, as is disclosed in U.S. Pat. No. 4,548,779 to Steinberg et al.

SUMMARY OF THE INVENTION

It is an object of the present invention to provide a method of inhibiting the growth of algae and like organisms in water tanks. It is a further object of the present invention to provide such a method utilizing a tank having an outer surface operative to reflect sunlight and reduce the amount of heat absorbed by the tank, and having an opaque layer that prevents sunlight from passing through the tank to the water stored therein.

It is a further object of the present invention to provide such a tank comprising a layered wall. An exterior layer of the wall is of a natural or light color and an interior layer of the wall is dark pigmented, such as black.

The invention provides a plastic water storage tank that provides the light reflecting properties of a light colored tank, which reflection thereby reduces the amount of heat generated in the plastic tank, but which also is opaque and thus provides the sunlight-blocking properties of a dark colored tank.

The present invention provides, in one embodiment, a method of inhibiting the growth of algae in plastic water tanks exposed to sunlight. The method comprises providing an outer tank surface operative to reflect off a substantial portion of sunlight that strikes the outer tank surface; and providing an opaque inner tank layer operative to substantially prevent sunlight passing through the outer tank surface from entering an interior of the tank.

In a second embodiment the invention provides a plastic water tank operative to inhibit the growth of algae in water stored in the plastic tank when exposed to sunlight. The tank comprises an outer tank surface operative to reflect off a substantial portion of sunlight that strikes the outer tank surface. An opaque inner tank layer is operative to substantially prevent sunlight passing through the outer tank surface from entering an interior of the tank and encouraging growth of algae in water stored therein.

Conveniently the outer surface of the tank is provided by the outer surface of a light colored outer tank layer.

In this way a tank is provided which requires no greater wall thickness than a conventional light colored tank while providing the algae growth-inhibiting benefits of a dark colored tank. The cost is reduced compared to a conventional dark colored tank which requires a thicker wall to resist deformity. The tank is conveniently made by a rotational molding process.

DESCRIPTION OF THE DRAWINGS

While the invention is claimed in the concluding portions hereof, preferred embodiments are provided in the accompanying detailed description which may be best understood in conjunction with the accompanying diagrams where like parts in each of the several diagrams are labeled with like numbers, and where:

DETAILED DESCRIPTION OF THE ILLUSTRATED EMBODIMENTS

Figure 1:
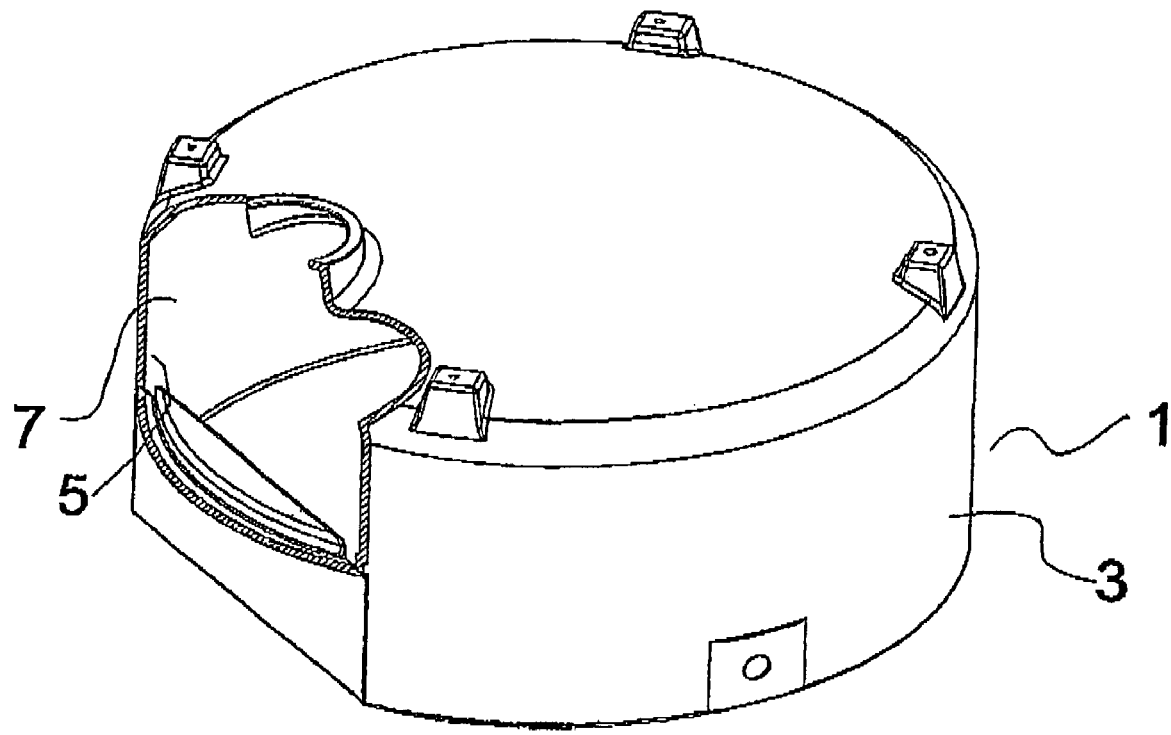
FIG. 1 is a perspective cut-away view of a tank embodying the invention.

FIG. 1 illustrates a plastic water tank 1 operative to inhibit the growth of algae in water stored in the tank 1 when exposed to sunlight. The tank 1 has an outer tank surface 3 operative to reflect off a substantial portion of sunlight that strikes the outer tank surface 3 and also has an opaque inner tank layer 5 operative to substantially prevent sunlight passing through the light colored outer tank surface 3 from entering an interior 7 of the tank 1.

By reflecting off a substantial portion of the sunlight, the amount of heat generated in the plastic of the tank 1 is reduced, such that softening of the plastic and the risk of resulting deformity of the tank 1 is reduced. The reflective outer surface could be provided by painting the outer surface with a light colored or white paint, however it is difficult to keep such paint in place on plastic surfaces.

Figure 2:
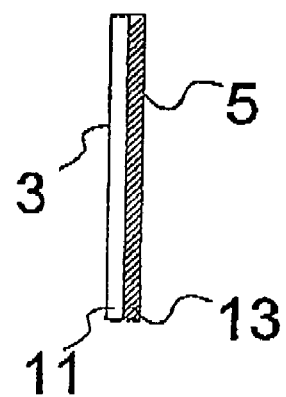
FIG. 2 is a schematic cross-sectional view of a wall of the tank of FIG. 1.

FIG. 2 illustrates a schematic section of an embodiment having a tank wall wherein the outer tank surface 3 of the tank 1 is provided by a light colored outer tank layer 11 and the opaque inner tank layer 5 is provided by a dark colored inner tank layer 13 adhered to an inner surface of the light colored outer tank layer 11. Conveniently the tank 1 is rotationally molded by placing light colored resin granules into a rotational mold and heating and turning the rotational mold to melt the light colored resin granules and form the light colored outer tank layer 11. After the light colored resin granules have been melted to form the light colored outer tank layer 11, dark colored resin granules are added into the rotational mold and the rotational mold is heated and turned to melt the dark colored resin granules and form the dark colored inner tank layer 13.

The tank 1 could also be rotationally molded by placing light colored resin granules into a rotational mold and heating and turning the rotational mold to melt a first portion of the light colored resin granules and form the light colored outer tank layer 11, and after the first portion of the light colored resin granules has been melted to form the light colored outer tank layer 11, adding dark colored pigment into the rotational mold and heating and turning the rotational mold to mix a second portion of the light colored resin granules and the dark colored pigment and melt the second portion of the light colored resin granules and form the dark colored inner tank layer 13. Typically about one half of the plastic granules would be used for each layer, making a tank 1 with layers 11, 13 of substantially equal thickness.

The granules or pigment can be added to the mold by a drop box or other method known in the rotational molding art for making multiple layered articles. It is also known to add two different plastic granules with different melting points to form a two-layered article.

With the tank 1 of the invention, the growth of algae is inhibited by preventing sunlight from entering the tank interior 7, while at the same time a substantial proportion of the sunlight that hits the tank 1 is reflected off, reducing heat build up in the plastic of the tank 1. The tank wall is thus substantially the same thickness as a conventional light colored tank. The cost of the tank 1 is thus less than a conventional sun-blocking dark tank which requires a thicker wall to maintain its structure when exposed to sunlight, and only marginally more than a conventional tank made entirely of light colored plastic.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

What is claimed is:

1. A method of rotationally molding a plastic water tank operative to inhibit the growth of algae when exposed to sunlight, the method comprising:

heating and turning a rotational mold to melt a first portion of resin granules and form a light colored outer tank layer of the tank having an outer surface operative to reflect off a substantial portion of sunlight that strikes the outer tank surface; and after forming the light colored outer tank layer, heating and turning the rotational mold to melt a second portion of resin granules and form a dark colored inner tank layer of the tank operative to substantially prevent sunlight passing through the outer tank surface from entering an interior of the tank.

2. The method of claim 1 wherein the first and second portions of resin granules are light colored and are placed into the rotational mold and the rotational mold is heated and turned to melt the first portion of light colored resin granules and form the light colored outer tank layer and, after the first portion of light colored resin granules have been melted to form the light colored outer tank layer, dark colored pigment is placed into the rotational mold and the rotational mold is heated and turned to mix and melt the second portion of the light colored resin granules and the dark colored pigment and form the dark colored inner tank layer.

3. The method of claim 1 wherein the first portion of resin granules are light colored resin granules and are placed into the rotational mold and the rotational mold is heated and turned to melt the light colored resin granules and form the light colored outer tank layer and, after the light colored resin granules have been melted to form the light colored outer tank layer, dark colored resin granules are placed into the rotational mold and the rotational mold is heated and turned to melt the dark colored resin granules and form the dark colored inner tank layer.

4. The method of claim 1 wherein the outer and inner tank layers together provide a wall thickness that is substantially equal to a wall thickness of a conventional plastic water tank made with a single light colored tank layer and having substantially the same dimensions.

\* \* \* \* \*